US011522722B2

(12) United States Patent
Suzuki

(10) Patent No.: US 11,522,722 B2
(45) Date of Patent: Dec. 6, 2022

(54) COMMUNICATION APPARATUS AND COMMUNICATION METHOD

(71) Applicant: FUJITSU LIMITED, Kawasaki (JP)

(72) Inventor: Dai Suzuki, Kawasaki (JP)

(73) Assignee: FUJITSU LIMITED, Kawasaki (JP)

(*) Notice: Subject to any disclaimer, the term of this patent is extended or adjusted under 35 U.S.C. 154(b) by 199 days.

(21) Appl. No.: 16/990,125

(22) Filed: Aug. 11, 2020

(65) Prior Publication Data
US 2021/0067351 A1 Mar. 4, 2021

(30) Foreign Application Priority Data
Sep. 3, 2019 (JP) .............................. JP2019-160133

(51) Int. Cl.
H04L 9/32 (2006.01)
H04L 29/06 (2006.01)
G06F 16/182 (2019.01)
G06F 21/62 (2013.01)

(52) U.S. Cl.
CPC ........ H04L 9/3268 (2013.01); G06F 16/1827 (2019.01); G06F 21/6254 (2013.01)

(58) Field of Classification Search
CPC . H04L 9/3268; G06F 16/1827; G06F 21/6254
See application file for complete search history.

(56) References Cited

U.S. PATENT DOCUMENTS

| 10,936,422 | B1* | 3/2021 | Paczkowski | ........ G06F 11/1417 |
| 2004/0236748 | A1* | 11/2004 | Coltrera | ................. G16H 10/20 |
| | | | | 707/999.009 |
| 2009/0320095 | A1 | 12/2009 | Nanda et al. | |
| 2014/0281503 | A1* | 9/2014 | Mills | ..................... H04L 9/3268 |
| | | | | 713/157 |

(Continued)

FOREIGN PATENT DOCUMENTS

JP  2011-525028 A   9/2011
WO  2009/155129 A2  12/2009

OTHER PUBLICATIONS

Hasavari Shirin et al.,"A secure and Scalable Data Source for Emergency Medical Gare using Blockchain Technology", 2019 IEEE 17th International Conference on Software Engineering Research, Management and Applications (SERA), IEEE, May 29, 2019, pp. 71-75, XP033653588, [retrieved on Oct. 29, 2019].

(Continued)

Primary Examiner — Darshan I Dhruv
(74) Attorney, Agent, or Firm — Fujitsu Patent Center

(57) ABSTRACT

A communication apparatus configured to acquire information in a distributed ledger shared in a network, the communication apparatus includes a memory; and a processor coupled to the memory and configured to acquire one or more digital certificates used by a user of another apparatus to apply to the communication apparatus from the other apparatus, acquire type information that identifies a combination of the user and the type of information certified by the one or more digital certificates, by using the distributed (Continued)

ledger, acquire certificate issue history that is recorded in the distributed ledger in association with the type information, and determine whether the issue history contains information of another digital certificate that has not been acquired from the other apparatus.

6 Claims, 15 Drawing Sheets

(56) References Cited

U.S. PATENT DOCUMENTS

| | | | | |
|---|---|---|---|---|
| 2014/0325209 | A1* | 10/2014 | Koster | H04L 63/0823 726/10 |
| 2016/0125045 | A1* | 5/2016 | Unagami | H04L 63/101 707/722 |
| 2019/0140844 | A1* | 5/2019 | Brown | H04L 63/0823 |
| 2019/0251573 | A1* | 8/2019 | Toyota | H04L 9/3236 |
| 2019/0266312 | A1* | 8/2019 | Mintz | G06F 21/645 |
| 2019/0266597 | A1 | 8/2019 | Mohtar | |
| 2019/0268140 | A1 | 8/2019 | Kandiraju et al. | |
| 2019/0280882 | A1* | 9/2019 | Kodera | G06F 21/33 |
| 2020/0151708 | A1* | 5/2020 | Sui | H04L 9/14 |
| 2020/0394675 | A1* | 12/2020 | Bradford | G06Q 30/0269 |
| 2021/0058786 | A1* | 2/2021 | Yang | H04L 9/3263 |
| 2021/0334363 | A1* | 10/2021 | Kim | G06F 21/54 |

OTHER PUBLICATIONS

Lijng Zhou et al.,"MIStore: a Blockchain-Based Medical Insurance Storage System", Journal of Medical Systems., vol. 42, No. 8, Jul. 2, 2018, XP055573867. Cited in EESR dated Jan. 27, 2021 corresponding to European Patent Application No. 20190697.1.

EESR—Extended European Search Report dated Jan. 27, 2021 for corresponding European Patent Application No. 20190697.1.

* cited by examiner

FIG. 4

| COMMUNICATION APPARATUS | APPARATUS ID | PUBLIC KEY | ADDRESS |
|---|---|---|---|
| COMMUNICATION APPARATUS 10a | IDA | KeyPA | IPa |
| COMMUNICATION APPARATUS 10b | IDB | KeyPB | IPb |
| COMMUNICATION APPARATUS 10c | IDC | KeyPC | IPc |
| COMMUNICATION APPARATUS 10d | IDD | KeyPD | IPd |
| ..... | ... | ... | ... |

FIG. 9

|  | SECRET KEY | PUBLIC KEY |
|---|---|---|
| MEDICAL HISTORY | KeyA | KeyB |
| EDUCATIONAL ATTAINMENT | KeyC | KeyD |
| ... | ..... | ... |

COMMUNICATION APPARATUS AND COMMUNICATION METHOD

CROSS-REFERENCE TO RELATED APPLICATION

This application is based upon and claims the benefit of priority of the prior Japanese Patent Application No. 2019-160133, filed on Sep. 3, 2019, the entire contents of which are incorporated herein by reference.

FIELD

The embodiments discussed herein are related to a communication apparatus and a communication method.

BACKGROUND

When using various services such as application for a credit card, opening a bank account, and buying insurance, a service user sometimes presents a digital certificate to a service provider. A digital certificate may be issued by a certificate authority. In this case, the certificate authority performs identity confirmation and the like for a user and issues a certificate based on the result. The user presents the obtained digital certificate to the service provider.

In recent years, a distributed ledger technology that has emerged as a platform for realizing virtual currency has attracted attention. The use of a distributed ledger may suppress information from being tampered with without the presence of a central administrator of the system, and application to areas other than virtual currency is also being studied.

As a related technique, a method for obtaining a token for accessing a service of a relying party from an identity provider is known (for example, Japanese National Publication of International Patent Application No. 2011-525028).

SUMMARY

According to an aspect of the embodiments, a communication apparatus configured to acquire information in a distributed ledger shared in a network, the communication apparatus includes a memory; and a processor coupled to the memory and configured to acquire one or more digital certificates used by a user of another apparatus to apply to the communication apparatus from the other apparatus, acquire type information that identifies a combination of the user and the type of information certified by the one or more digital certificates, by using the distributed ledger, acquire certificate issue history that is recorded in the distributed ledger in association with the type information, and determine whether the issue history contains information of another digital certificate that has not been acquired from the other apparatus.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 4 is a diagram describing an example of a public key information contained in a distributed ledger;

FIG. 9 is a diagram describing an example of key information used for encrypting category ID;

DESCRIPTION OF EMBODIMENTS

Figure 1:
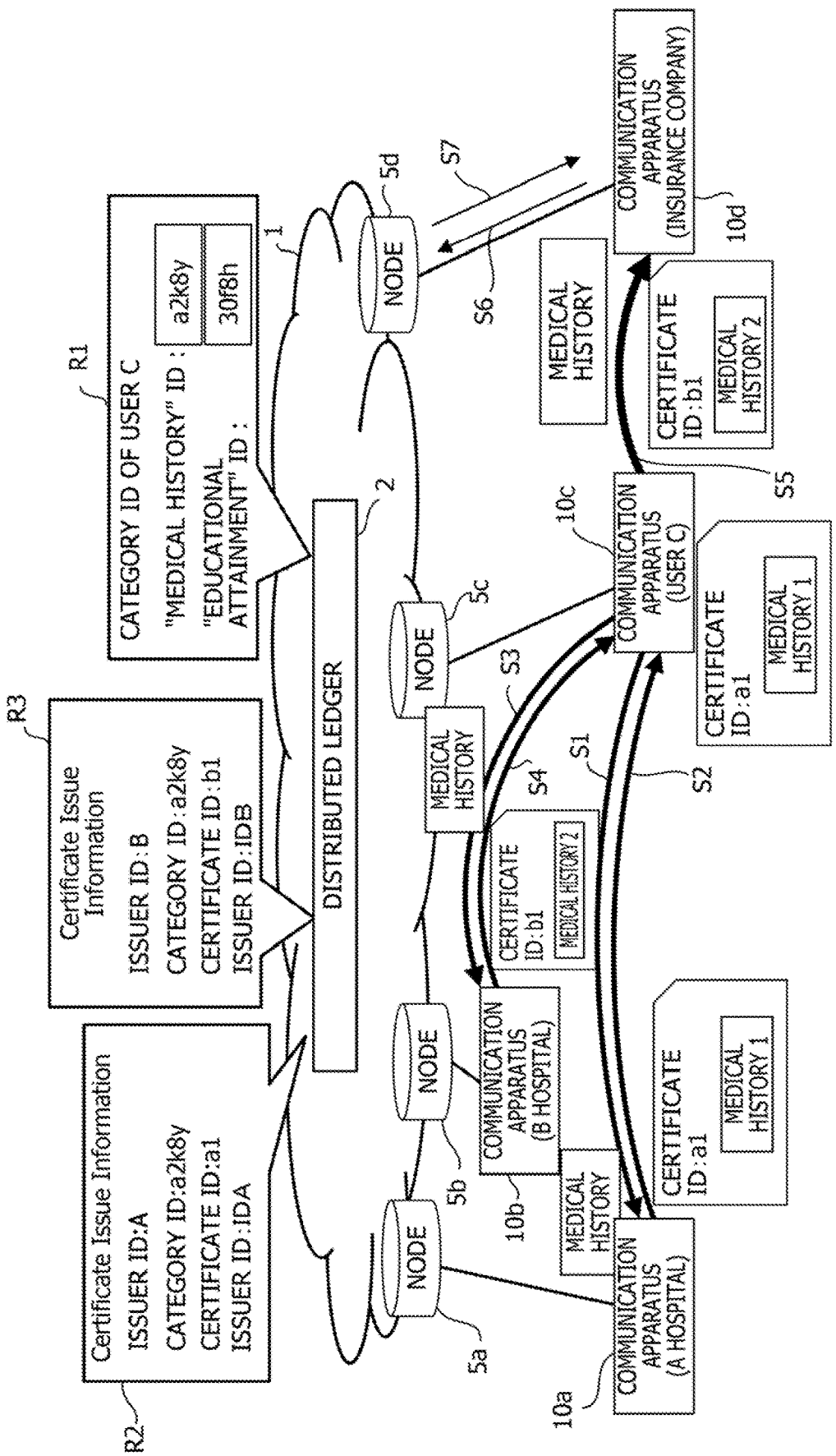
FIG. 1 is a diagram describing an example of a communication method according to an embodiment.

FIG. 1 is a diagram describing an example of a communication method according to an embodiment. In the example illustrated in FIG. 1, nodes 5 (5a to 5d) have participated in a network 1. The nodes 5a to 5d having participated in the network 1 are supposed to share a distributed ledger 2. The network 1 is a network of any desired form that allows the distributed ledger 2 to be shared. For example, the network 1 may be a consortium in the blockchain technology. In the example of FIG. 1, communication apparatuses 10 (10a to 10d) are coupled to the nodes 5. Each communication apparatus 10 is supposed to be able to acquire information in the distributed ledger 2 through the node 5 to which the communication apparatus 10 is coupled.

Hereinafter, with reference to FIG. 1, an example in which the service to be provided is insurance, and the certificate is a medical history certificate of a user is described. It is supposed that the communication apparatus 10a is a communication apparatus 10 installed in an A hospital and the communication apparatus 10b is a communication apparatus 10 installed in a B hospital. It is supposed that the communication apparatus 10c is an apparatus used by a user C who is about to use the insurance, and the communication apparatus 10d is a communication apparatus 10 used by an insurance company. It is supposed that the identification information (issuer ID) of the A hospital as an issuer of the certificate is IDA, and the issuer ID of the B hospital is IDB.

First, upon receipt of an input of a category of which to acquire a certificate, the communication apparatus 10c generates identification information (type information) which is capable of uniquely specifying a combination of the category (type) and the user C using the communication apparatus 10c. In the following description, the identification information which is capable of uniquely specifying the combination of a category and a user is sometimes described as "category ID". The communication apparatus 10c notifies the node 5c of the generated category ID. The node 5c then registers the received category ID into the distributed ledger 2. In the example of FIG. 1, as indicated in R1, a2k8y as the category D on the medical history of the user C and 30f8h as the category ID on the educational attainment of the user C are registered in the distributed ledger 2. The information of the category ID on the user C is shared between the nodes 5, which share the distributed ledger 2. Each communication apparatus 10 is also capable of acquiring the category ID through the node 5.

Next, the user C transmits a request for the medical history certificate from the communication apparatus 10c to the communication apparatus 10a in order to acquire the medical history certificate from the A hospital (step S1). The operator of the communication apparatus 10a is supposed to have generated a medical history certificate C1 of the user C. The communication apparatus 10a generates issue information on the certificate C1 and transmits the issue information to the node 5a. The issue information on the certificate C1 contains the category ID that specifies the medical history of the user C. As illustrated in R2, the node 5a records the received issue information in the distributed ledger 2. The record illustrated in the issue information R2 indicates that the certificate of certificate ID=a1 on the combination of the user and the category identified by the category ID=a2k8y from the issuer ID=IDA (A hospital). Thereafter, the certificate of certificate ID=a1 is transmitted from the communication apparatus 10a to the communication apparatus 10c (step S2).

In the case where the user C acquires the medical history certificate from the B hospital as well, the same processing as in the acquisition of the certificate from the A hospital is conducted. Specifically, for example, a request for the medical history certificate is transmitted from the communication apparatus 10c to the communication apparatus 10b (step S3). Since the same processing as in the communication apparatus 10a is conducted by the communication apparatus 10b, information of the certificate generated by the communication apparatus 10b is also registered in the distributed ledger 2 by the node 5b. Hence, as indicated in R3, the fact that the certificate of certificate ID=b1 has been issued for the combination of the user and the category identified by category ID=a2k8y from issuer ID=IDB (B hospital) is recorded in the distributed ledger 2. Thereafter, the certificate of certificate ID=b1 is transmitted from the communication apparatus 10b to the communication apparatus 10c (step S4).

Next, for the application for use of a service by the user C, the communication apparatus 10c sends information indicating that the certificate and the category of the certificate are for the medical history to the communication apparatus 10d (step S5). In the example of FIG. 1, it is supposed that the communication apparatus 10c has transmitted both of the certificate acquired by the user C from the A hospital and the certificate acquired by the user C from the B hospital to the communication apparatus 10d.

The communication apparatus 10d requests a certificate issue history of the medical history certificates of the user C from the node 5d (step S6). The "certificate issue history" is a list of identification information of all certificates issued for a certain category to a certain user.

The node 5d refers to the record of R1 in the distributed ledger 2 to recognize that the category ID identifying the combination of the user C and the medical history is "a2k8y". The node 5d retrieves issue information that is recorded in the distributed ledger 2 in association with the category ID=a2k8y. In the example of FIG. 1, it is identified from issue information R2 and R3 that the certificates of certificate IDs=a1, b1 have been issued. The node 5d notifies the communication apparatus 10d of the certificate IDs=a1, b1 as the certificate issue history (step S7). The communication apparatus 10d compares the certificate ID received from the node 5d and the certificate ID contained in the certificate received from the communication apparatus 10c. In the example of FIG. 1, since the certificate ID received from the node 5d and the certificate ID contained in the certificate received from the communication apparatus 10c coincide with each other, the communication apparatus 10d may determine that the user C has submitted all the certificates acquired for the medical history.

Thereafter, the communication apparatus 10d verifies the certificates by decrypting each of the received certificates. For verifying a certificate, the communication apparatus 10d is supposed to be capable of acquiring a public key, which is paired with a secret key used in the apparatus that issued each certificate, as appropriate from the node 5d. The public key of each communication apparatus 10 is supposed to be registered in the distributed ledger 2 in advance. In the example of FIG. 1, the communication apparatus 10d may decrypt the certificate by acquiring the public key of the communication apparatus 10a associated with issuer ID=IDA and the public key of the communication apparatus 10b associated with issuer ID=IDB from the node 5d.

In a case where the communication apparatus 10 has not received 1 or more certificates identified by IDs contained in the certificate issue history, the communication apparatus 10 may determine that all the certificates have not transmitted from the user who is about to receive the service. In the case where 1 or more certificates identified by IDs contained in a certificate issue history have not been transmitted, the communication apparatus 10 may determine there is a possibility that the user who is about to receive a service might have hidden some of the certificates.

As described above, in the system using the communication method according to the embodiment, every time a certificate is issued, certificate issue information is recorded in the distributed ledger 2 in association with a category ID. Hence, issue information on all certificates is registered in the distributed ledger 2. Each certificate is issued after a user registers, in the distributed ledger 2, a category ID which is capable of uniquely specifying a combination of the user and the category of the certificate. This makes it possible for a service provider to identify whether a service user has submitted, to the provider, all digital certificates the user acquired for a category related to the service, by using the record of the distributed ledger 2.

FIG. 1 is a mere example, and the numbers of the nodes 5 and the communication apparatuses 10 in the network may be changed as desired. The types of certificates to be submitted and types of services to be provided may also be changed as desired depending on the implementation.

<Apparatus Configuration>

Figure 2:
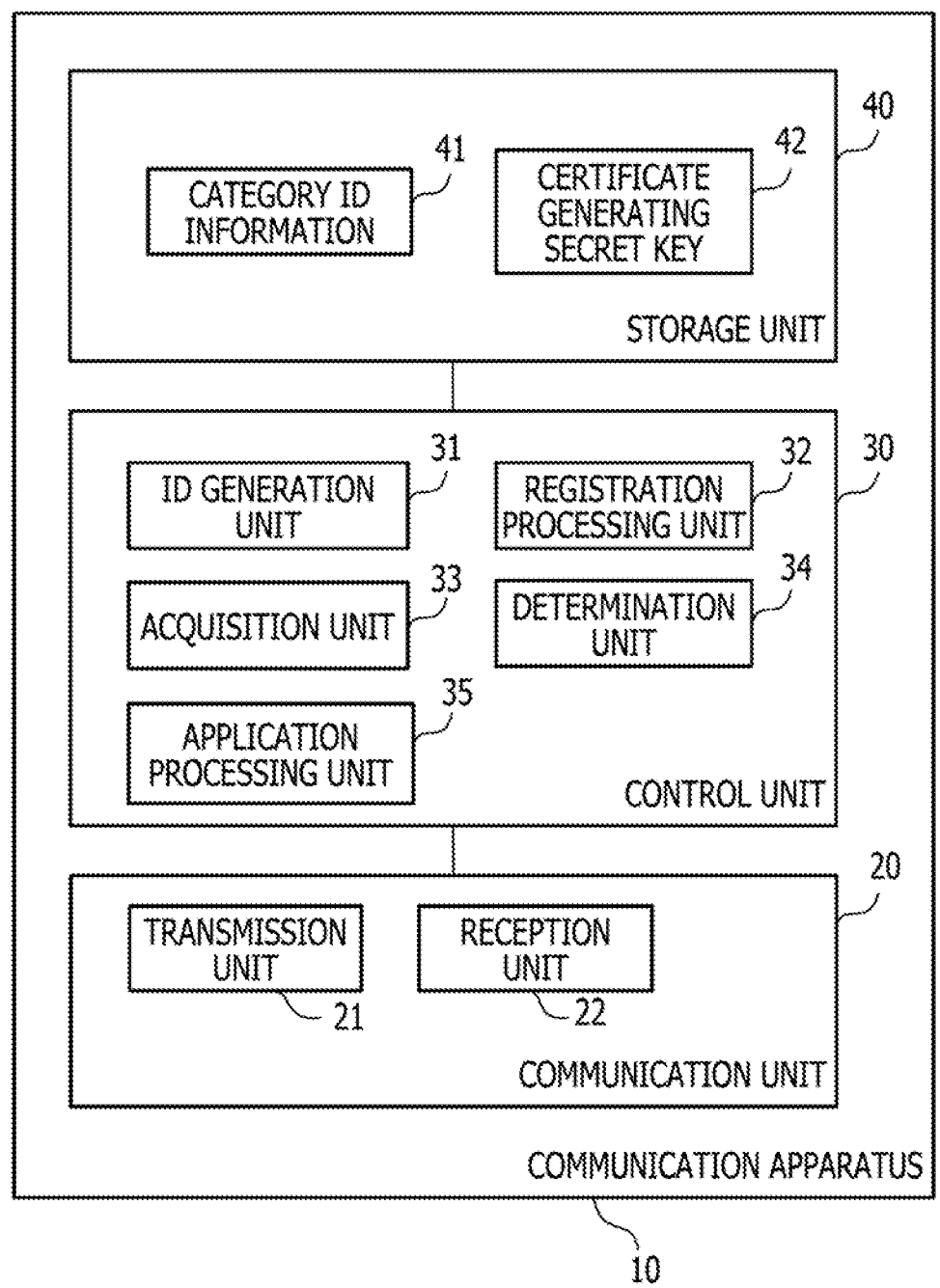
FIG. 2 is a diagram describing an example of a configuration of a communication apparatus.

FIG. 2 is a diagram describing an example of a configuration of the communication apparatus 10. The communication apparatus 10 includes a communication unit 20, a control unit 30, and a storage unit 40. The communication unit 20 includes a transmission unit 21 and a reception unit 22. The transmission unit 21 transmits packets to the node 5, another communication apparatus 10, and the like. The reception unit 22 receives packets from the node 5, another communication apparatus 10, and the like.

The control unit 30 includes an ID generation unit 31, a registration processing unit 32, an acquisition unit 33, a determination unit 34, and an application processing unit 35. The ID generation unit 31 generates category ID. The ID generation unit 31 is used in a case where the communication apparatus 10 operates as a terminal of the user who acquires a certificate. The registration processing unit 32 conducts processing for registering, in the distributed ledger 2, information such as category ID and certificate issue information. For example, the registration processing unit 32 transmits information to be registered into the distributed ledger 2 to the node 5 to which the communication apparatus 10 is coupled, and conducts processing for requesting for registration into the distributed ledger 2. The acquisition unit 33 conducts processing for acquiring information from the node 5. For example, the acquisition unit 33 is used in the case where the communication apparatus 10 operates as an apparatus that issues a certificate or an apparatus that verifies a certificate. The determination unit 34 determines whether there is a possibility that a certificate has been hidden, by comparing certificate ID contained in the certificate issue history and certificate ID contained in a received digital certificate. The application processing unit 35 conducts processing by an application operating in the communication apparatus 10. For example, the application processing unit 35 issues a digital certificate, verifies a digital certificate by using the application, and conducts other processing.

The storage unit 40 stores category ID information 41 and a certificate generating secret key 42. The category ID information 41 is information of category ID generated by the communication apparatus 10. The certificate generating secret key 42 is a secret key used for encrypting a generated certificate in a case where the communication apparatus 10 operates as an apparatus that issues a certificate.

Figure 3:
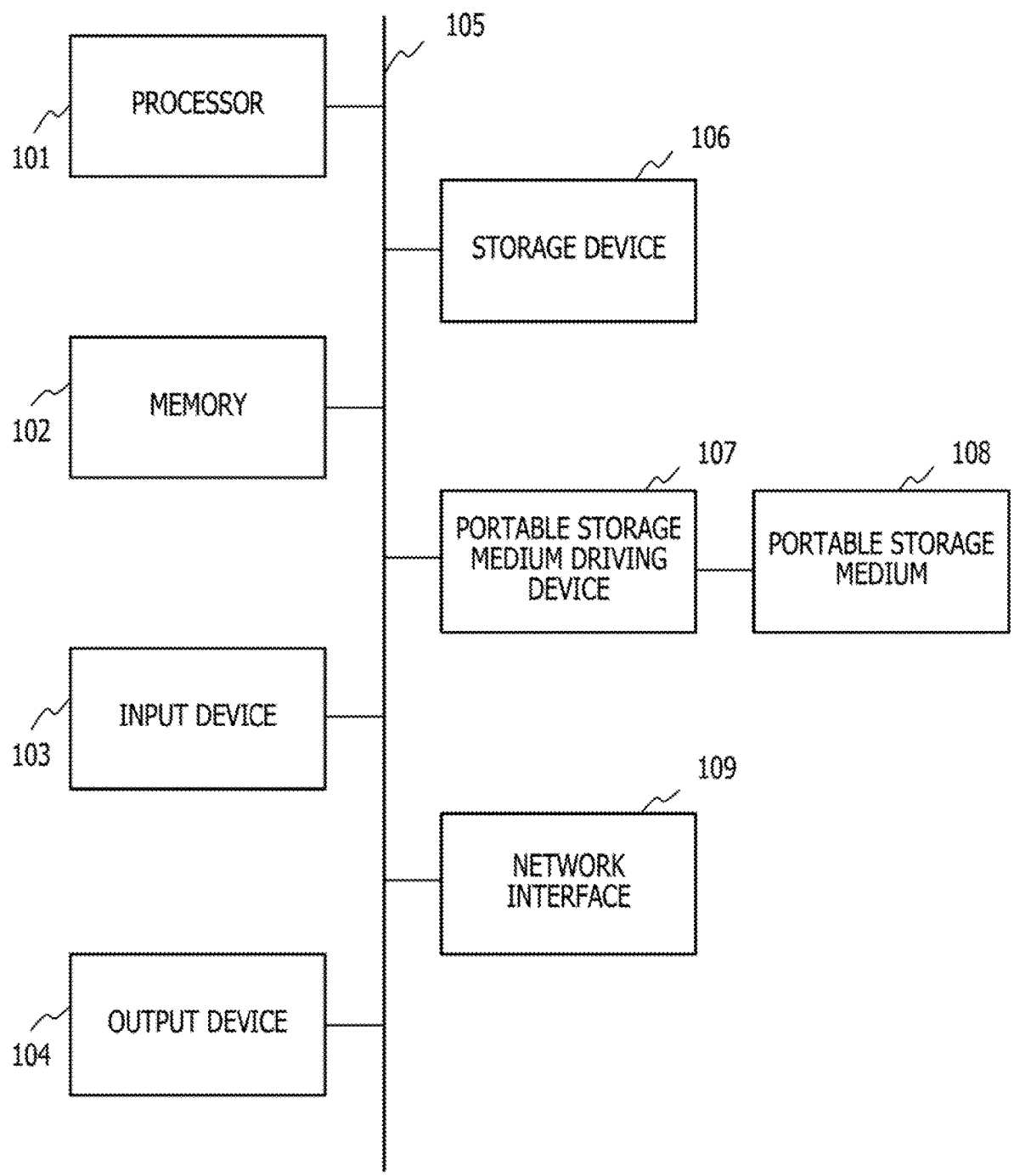
FIG. 3 is a diagram describing an example of a hardware configuration of a communication apparatus.

FIG. 3 is a diagram describing an example of a hardware configuration of the communication apparatus 10. The communication apparatus 10 includes a processor 101, a memory 102, a bus 105, and a network interface 109. The communication apparatus 10 may further include at least one of an input device 103, an output device 104, a storage device 106, and a portable storage medium driving device 107.

The processor 101 is any processing circuit, and may be, for example, a central processing unit (CPU). The processor 101 operates as the control unit 30. The processor 101 is able to execute programs stored in the memory 102, the storage device 106, and the like. The memory 102 appropriately stores data acquired by the operation of the processor 101 and data used for the processing of the processor 101. The storage device 106 stores programs, data, and the like, and provides the stored information to the processor 101 or the like, as appropriate. The memory 102, the storage device 106, and the like operate as the storage unit 40 in the communication apparatus 10.

The bus 105 couples the processor 101, the memory 102, the input device 103, the output device 104, the storage device 106, the portable storage medium driving device 107, and the network interface 109 to each other so that the data is able to be transmitted and received to and from each other. The input device 103 is any device used to input information, such as a keyboard, a mouse, a microphone, or a camera, and the output device 104 is any device used to output data, such as a display. The portable storage medium driving device 107 is able to output data in the memory 102, the storage device 106, and the like to a portable storage medium 108 and is able to read out programs, data, and the like from the portable storage medium 108. The portable storage medium 108 may be any portable storage medium including a compact disc recordable (CD-R) and a digital versatile disk recordable (DVD-R). The network interface 109 carries out processing of making the communication apparatus 10 communicate with other apparatuses as appropriate. The network interface 109 operates as the communication unit 20.

First Embodiment

Hereinafter, a first embodiment is described separately from examples of information shared using the distributed ledger 2, the registration of category ID, the issue processing of a digital certificate, to the verification processing conducted in the communication apparatus 10 that has received a digital certificate. In the following example as well, the case where the certificate is a medical history certificate of a user. It is supposed that the communication apparatus 10a is a communication apparatus 10 installed in an A hospital and the communication apparatus 10b is a communication apparatus 10 installed in a B hospital. It is supposed that the communication apparatus 10c is an apparatus used by a user C who is about to use the insurance, and the communication apparatus 10d is a communication apparatus 10 used by an insurance company.

In the following description, in order to clarify the communication apparatus 10 that is conducting the processing, the alphabet at the end of the reference sign of the communication apparatus 10 that is conducting the processing may be added at the end of the reference sign of the portion of the communication apparatus 10. For example, the ID generation unit 31a is an ID generation unit 31 of the communication apparatus 10a, and the registration processing unit 32c is a registration processing unit 32 of the communication apparatus 10c.

FIG. 4 is a diagram describing an example of the public key information contained in the distributed ledger 2. In the distributed ledger 2, not only information such as category ID and the certificate issue information but also public key information is also held, as described with reference to FIG. 1. The public key information is information on a public key paired with a secret key used for encrypting a certificate in each communication apparatus 10.

The public key information illustrated in FIG. 4 is associated with a communication apparatus, apparatus ID, a public key, and an address. The apparatus ID is identification information assigned to the communication apparatus 10 in the entry. The public key is a public key paired with a secret key used by the communication apparatus 10 in the entry for encryption. The address is an address assigned to the communication apparatus 10 in the entry. For example, apparatus ID=IDA and address=IPa are assigned to the communication apparatus 10a, and the public key paired with the secret key used by the communication apparatus 10a is KeyPA. Apparatus ID=IDB and address=IPb are assigned to the communication apparatus 10b, and the public key paired with the secret key used by the communication apparatus 10b is KeyPB. Similarly, apparatus ID=IDC and address=IPc are assigned to the communication apparatus 10c, and the public key paired with the secret key used by the communication apparatus 10c is KeyPC. Apparatus ID=IDD and address=IPd are assigned to the communication apparatus 10d, and the public key paired with the secret key used by the communication apparatus 10d is KeyPD.

Figure 5:
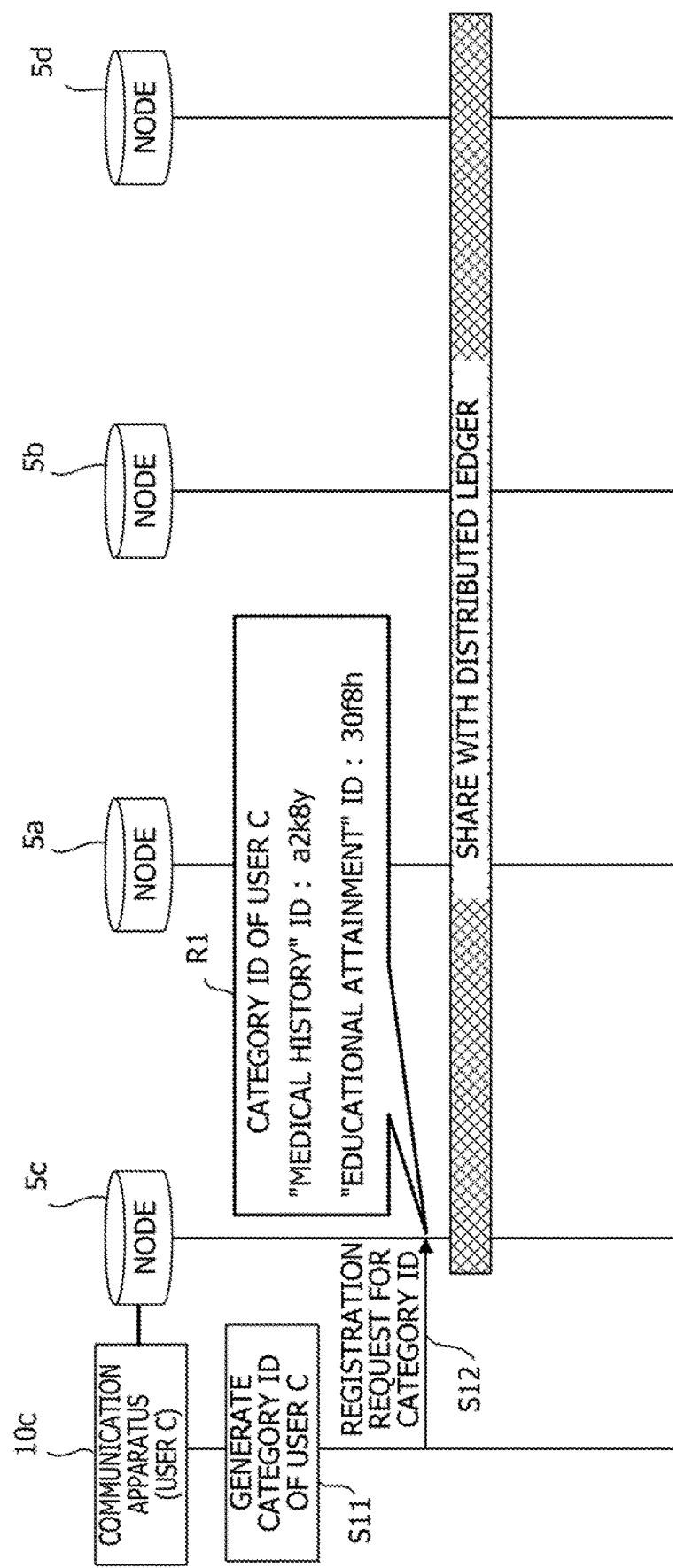
FIG. 5 is a sequence diagram describing an example of registration processing for category ID.

FIG. 5 is a sequence diagram describing an example of registration processing for category ID. With reference to FIG. 5, an example of processing in the case where category ID which the user C uses for acquiring a certificate is registered in the distributed ledger 2 is described.

The ID generation unit 31c of the communication apparatus 10c generates category ID which is capable of uniquely specifying the combination of the user C and the category (step S11). The method of generating category ID may be any known method. In the example of FIG. 5, in order for the user C to acquire the medical history certificate, the ID generation unit 31c is supposed to have generated a2k8y as category ID (medical history ID) which is capable of uniquely specifying the combination of the user C and the medical history. In order for the user C to acquire the educational attainment certificate, the ID generation unit 31c is supposed to have generated 30f8h as category ID (educational attainment ID) which is capable of uniquely specifying the combination of the user C and the medical history. In the following description, in order to make it easy to understand with which category each category ID is associated, category ID of each category is sometimes expressed with ID attached to the name of the category. For example, category ID which is capable of uniquely specifying the combination of the user C and the medical history is sometimes described as "medical history ID" of the user C. Similarly, category ID that is capable of uniquely specifying the combination of the user C and the educational attainment is sometimes described as "educational attainment ID" of the user C.

The registration processing unit 32c of the communication apparatus 10c requests the node 5c to register category ID generated by the ID generation unit 31c into the distributed ledger 2 (step S12). The node 5c records each of category IDs requested to be registered into the distributed ledger 2 in association with each category and information on the user. Hence, the information indicated in R1 of FIG. 5 is shared among the nodes 5a to 5d using the distributed ledger 2.

The record R1 indicated in FIG. 5 is one example of registration of category IDs and the form of registration may be changed depending on the implementation. For example, in the case where the communication apparatus 10 and the user are in one-to-one correspondence, category ID may be generated as information which is capable of uniquely specifying the combination of identification information of the communication apparatus 10 used by the user and the category. In this case, in the distributed ledger 2 as well, category ID may be recorded in association with the combination of the identification information of the communication apparatus 10 and the category.

Figure 6:
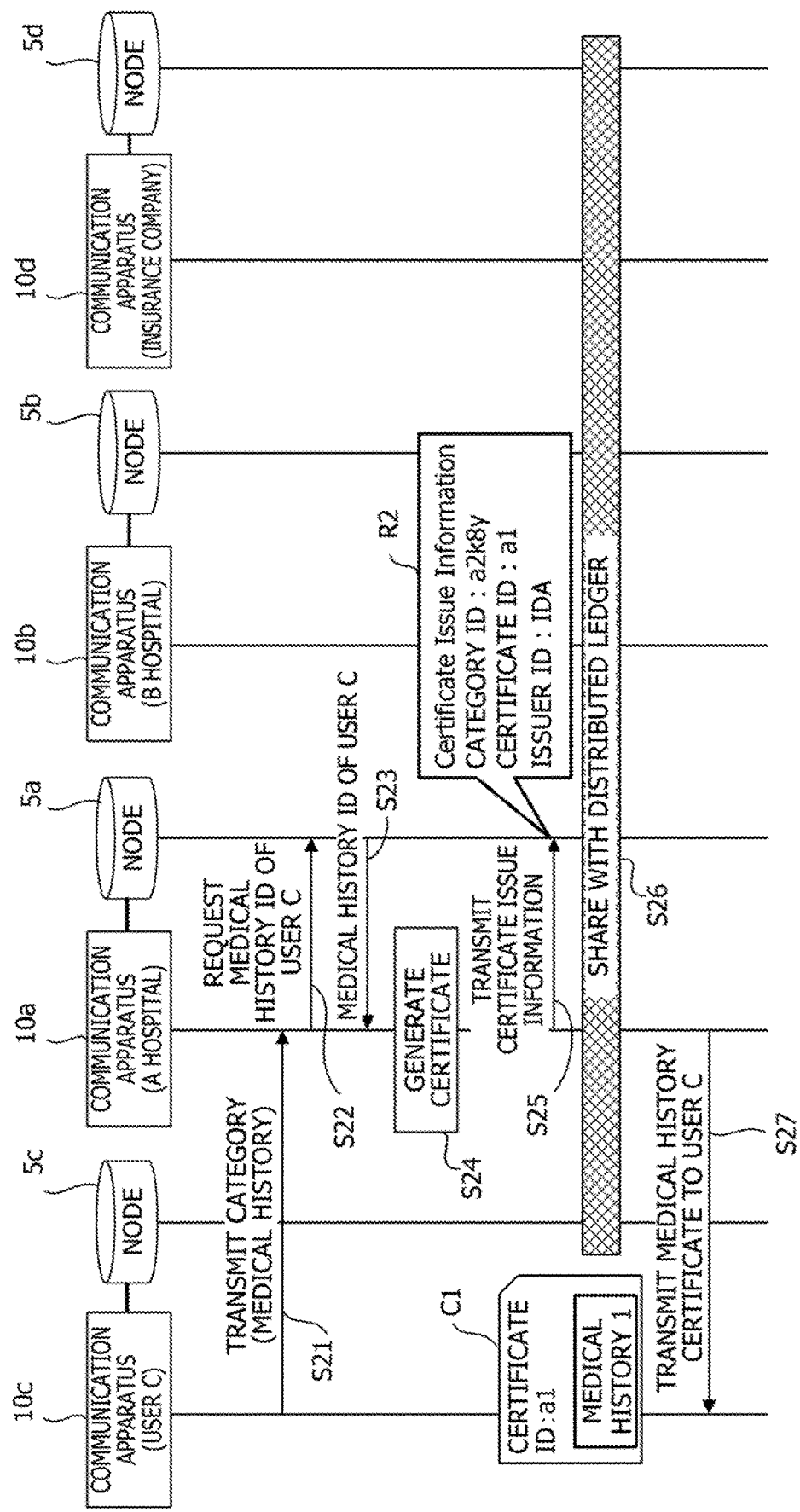
FIG. 6 is a sequence diagram describing an example of processing conducted when a certificate is issued.

FIG. 6 is a sequence diagram describing an example of processing conducted when a certificate is issued. With reference to FIG. 6, an example of processing in the case where the medical history certificate of the user C is issued by the communication apparatus 10a of the A hospital is described. It is supposed that the registration processing described with reference to FIG. 5 has been conducted before the processing of FIG. 6.

The application processing unit 35c of the communication apparatus 10c recognizes that acquisition of the medical history certificate from the A hospital has been requested by input from the user C or the like. The application processing unit 35c also recognizes that information such as an address of the communication apparatus 10a of the A hospital has also been acquired by the input from the user or the like. The application processing unit 35c generates a request message for a certificate containing information that the certificate of the user C is requested and that the category for requesting the certificate is the medical history. The transmission unit 21c transmits the generated request message to the communication apparatus 10a (step S21).

The acquisition unit 33a of the communication apparatus 10a acquires the request message through the reception unit 22a. The acquisition unit 33a then requests medical history ID of the user C from the node 5a (step S22). The node 5a recognizes that medical history ID of the user C is a2k8y by referring to the record R1 (FIG. 5) contained in the distributed ledger 2. The node 5a notifies the communication apparatus 10a of a2k8y as medical history ID of the user C (step S23).

The acquisition unit 33a of the communication apparatus 10a notifies the application processing unit 35a that the medical history certificate of the user C is requested and that category ID that specifies the medical history of the user C is a2k8y. The application processing unit 35a reads information on the medical history of the user C from the storage unit 40a and the like using the information received from the acquisition unit 33a to generate a medical history certificate C1 of the user C (step S24). The application processing unit 35a also generates certificate ID for identifying the generated certificate C1. In the example of FIG. 6, it is supposed that certificate ID of the certificate C1 generated by the application processing unit 35a on the medical history of the user C is a1.

The application processing unit 35a outputs certificate ID of the certificate C1 and the medical history ID of the user C to the registration processing unit 32a. The registration processing unit 32a requests the node 5a to record the combination of certificate ID and medical history ID received from the application processing unit 35a into the distributed ledger 2 as certificate issue information (step S25). The node 5a records the following information into the distributed ledger 2 as the certificate issue information (R2 of FIG. 6).

Certificate Issue Information
Category ID: a2k8y
Certificate ID: a1
Issuer ID: IDA The issuer ID is information for identifying the communication apparatus 10a that has issued the certificate C1. The information indicated in R2 of FIG. 6 is shared among the nodes 5a to 5d using the distributed ledger 2 by the registration processing of the node 5a (step S26).

The application processing unit 35a of the communication apparatus 10a encrypts the certificate C1 generated in step S24 with the certificate generating secret key 42a. It is supposed that certificate ID is recorded in a region that is not encrypted in the certificate. The application processing unit 35a outputs the encrypted certificate C1 and information indicating that the destination of the certificate C1 is the communication apparatus 10c to the transmission unit 21a. The transmission unit 21a transmits the certificate C1 inputted from the application processing unit 35a to the communication apparatus 10c (step S27). The communication apparatus 10c stores data of the certificate received through the reception unit 22c into the storage unit 40c as appropriate. Data of a certificate stored in the storage unit 40c is data encrypted at the issuer of the certificate.

Although the processing in the case where the communication apparatus 10a of the A hospital issues the medical history certificate C1 of the user C has been described with reference to FIG. 6, the generation of a certificate, the registration of certificate issue information, the transmission of a certificate may be conducted by the same processing in the other communication apparatuses 10 such as the communication apparatus 10b. The processing for any user other than the user C may be conducted in the same manner. The procedure of the processing described with reference to FIG.

6 is an example, and the procedure of the processing may be changed depending on the implementation. For example, the transmission processing of the certificate in step S27 may be conducted in parallel with the processing in steps S25, S26, or may be conducted before the processing in steps S25, S26.

Figure 7:
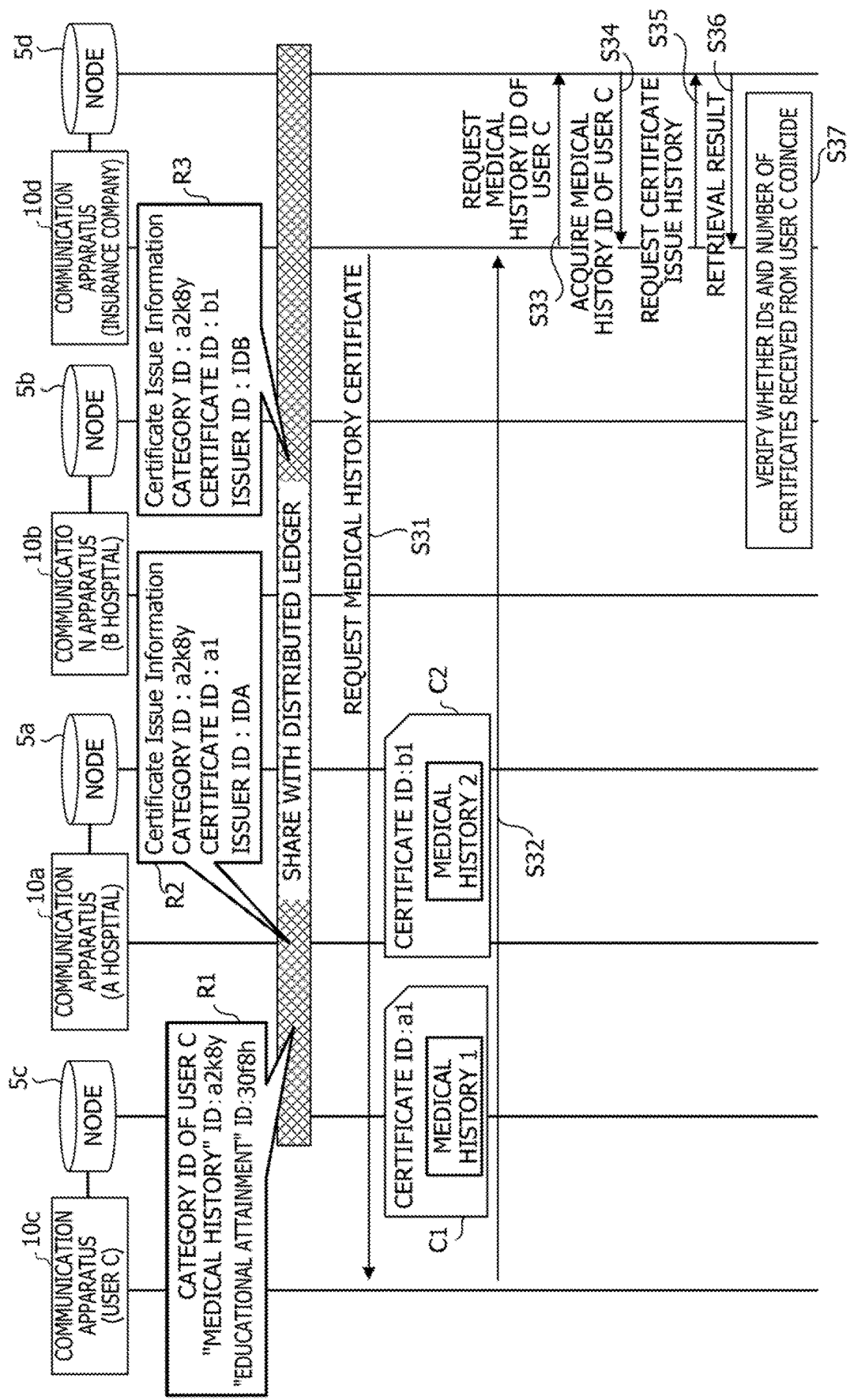
FIG. 7 is a sequence diagram describing an example of verification processing on completeness of a certificate.

FIG. 7 is a sequence diagram describing an example of the verification processing on completeness of a certificate. With reference to FIG. 7, an example of processing conducted in the case where the medical history certificates of the user C are issued from the A hospital and the B hospital, and the user C submits the medical history certificates to an insurance company is described. The processing of FIG. 7 is an example, and may be changed depending on the implementation.

It is supposed that at the time when the processing of FIG. 7 is conducted, category ID on the user C is registered in the distributed ledger 2 as indicated in the record R1 (FIG. 7) by the procedure described with reference to FIG. 5. It is also supposed that the issue information of the certificate C1 at the A hospital on the medical history of the user C is also registered in the distributed ledger 2 as indicated in the issue information R2 by the procedure described with reference to FIG. 6. It is also supposed that a certificate C2 is issued by the processing in the communication apparatus 10b and the node 5b used in the 8 hospital, and the following information is recorded in the distributed ledger 2 (R3 of FIG. 7).

Certificate Issue Information
Category ID: a2k8y
Certificate ID: b1
Issuer ID: IDB The information in the distributed ledger 2 is shared among the nodes 5a to 5d.

It is supposed that the user C applied for an insurance service to the insurance company. The operator of the insurance company transmits a send request for the medical history certificate from the communication apparatus 10d to the communication apparatus 10c used by the user C (step S31). The send request for a certificate may be conducted in any form. For example, the send request may be transmission of a mail requesting the user C to submit a certificate or transmission of information for displaying an operation screen through which a certificate may be sent on the communication apparatus 10c.

The reception unit 22c of the communication apparatus 10c receives the send request. In the case where the send request is data for displaying the operation screen on the communication apparatus 10c, the application processing unit 35c displays a display screen corresponding to the send request on the output device 104 (FIG. 3) such as a display. It is supposed that thereafter, the certificate C1 issued from the A hospital and the certificate C2 issued from the B hospital are transmitted to the communication apparatus 10d by the operation of the user C (step S32). It is supposed that both the certificates C1 and C2 transmitted to the communication apparatus 10d in step S32 have been transmitted to the communication apparatus 10d in the state of encrypted data encrypted at the issuer of the certificates.

It is supposed that the application processing unit 35d of the communication apparatus 10d has acquired data of the certificates C1, C2 and information indicating that these data are the medical history certificates of the user C through the reception unit 22d. The application processing unit 35d stores the obtained information into the storage unit 40 as appropriate. The acquisition unit 33d then inquires about medical history ID of the user C to the node 5d (step S33).

The node 5d acquires information, medical history ID of the user C=a2k8y, by referring to the distributed ledger 2 in accordance with the inquiry from the acquisition unit 33d of the communication apparatus 10d. The node 5d transmits the obtained medical history ID to the communication apparatus 10d (step S34).

The acquisition unit 33d of the communication apparatus 10d acquires the medical history ID of the user C=a2k8y through the reception unit 22d. Next, the acquisition unit 33d requests the node 5d for a certificate issue history of the certificate associated with the medical history ID of the user C (a2k8y) (step S35).

The node 5d retrieves certificate issue information associated with category ID=a2k8y in the distributed ledger 2 in response to the inquiry from the acquisition unit 33d of the communication apparatus 10d. In the example of FIG. 7, category ID=a2k8y is contained in the issue information R2 and the issue information R3. The node 5d then transmits the combination of the certificate information and issuer ID contained in the issue information retrieved to the communication apparatus 10d as certificate issue history (step S36). For example, in the example of FIG. 7, the following information is transmitted to the communication apparatus 10d as the certificate issue history.

Issue Information 1
Certificate ID=a1, issuer ID=IDA
Issue information 2
Certificate ID=b1, issuer ID=IDB The acquisition unit 33d of the communication apparatus 10d outputs the certificate issue history acquired from the node 5d through the reception unit 22d to the storage unit 40d and the determination unit 34d as appropriate. The determination unit 34d verifies whether ID and the number are coincident between the acquired certificate issue history and the certificates transmitted from the user (step S37). In the example of FIG. 7, the certificate C1 and the certificate C2 are transmitted from the user C to the communication apparatus 10d. The certificate C1 contains information that certificate ID=a1 and the certificate C2 contains information that certificate ID=b1. The determination unit 34d determines that IDs and the number contained in the certificates transmitted from the user C coincide with the certificate issue history received from the node 5d as information recorded in the distributed ledger 2. In this case, there is no possibility that the user C has hidden part of the certificates. Then, the operator of the communication apparatus 10d may conduct processing, such as decrypting each certificate and verifying the certificates after decryption, to provide the insurance service to the user C. The detail of acquisition of a public key and the like for verifying certificates is described with reference to FIG. 8.

Next, a case is described where in the processing of step S37, the determination unit 34d determines that IDs and the number of certificates are not coincide between the certificate issue history received from the node 5 and the certificates transmitted from the user. Each communication apparatus 10 that issues a certificate records the certificate issue information into the distributed ledger 2 through the node 5 when issuing a certificate. It is very difficult to tamper with the distributed ledger 2. Hence, it is certain that the certificate issue history received from the node 5 is a list completely covering all the certificates the user acquired for a specified category. For this reason, in the case where IDs and the number of certificates are not coincide between the certificate issue history received from the node 5 and the certificates transmitted from the user do not coincide, there is a possibility that the user has not transmitted part of the certificates or a possibility that the user has wrongly transmitted a certificate of another category. Hence, the communication method according to the first embodiment makes it possible for a service provider to specify that certificates are not properly submitted before decrypting each certificate or verifying the content of the certificate.

Figure 8:
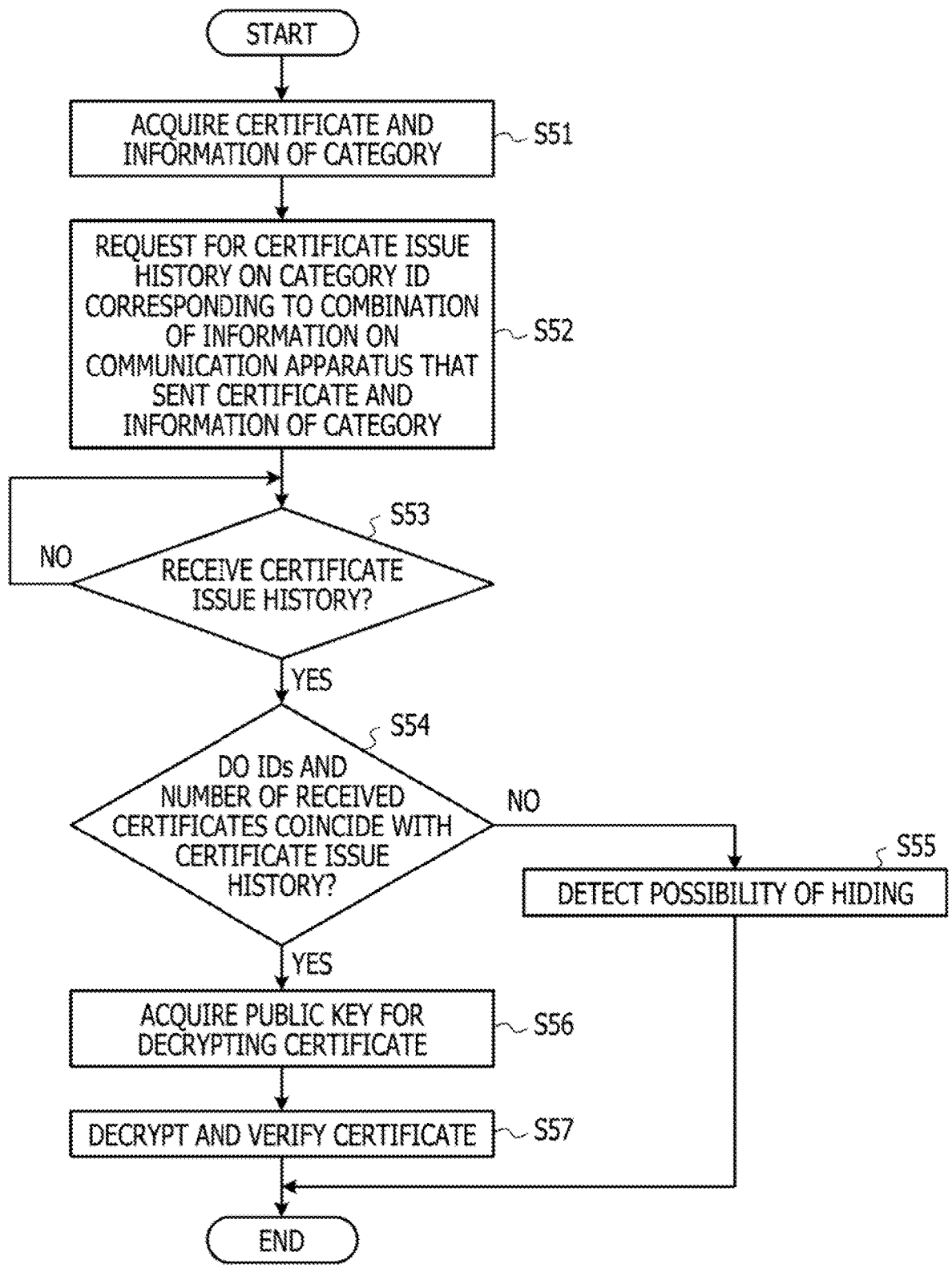
FIG. 8 is a flowchart describing an example of verification processing conducted by the communication apparatus.

FIG. 8 is a flowchart describing an example of verification processing conducted by the communication apparatus 10. FIG. 8 is an example of the processing, and may be changed depending on the implementation. For example, the processing in step S52 of FIG. 8 may be modified to two-time inquiry processing as indicated in steps S33 and S35 of FIG. 7. In the example of FIG. 8, category ID is generated in association with the combination of the communication apparatus 10 used by the user and the category, and is recorded in the distributed ledger 2.

The application processing unit 35 of the communication apparatus 10 acquires the certificate and information of the category (step S51). The application processing unit 35 stores the acquired information into the storage unit 40 as appropriate. The acquisition unit 33 requests the node 5 for the certificate issue history on the category ID corresponding to the combination of information on the communication apparatus 10 that sent the certificate and information of the category (step S52). The issue information is recorded in the distributed ledger 2 every time each certificate is issued, and it is very difficult to tamper with the distributed ledger 2. Hence, it is certain that the certificate issue history received from the node 5 is a list completely covering all the certificates the user acquired for the combination of the communication apparatus 10 used by the user and the category. The acquisition unit 33 stands by until acquiring the certificate issue history (No in step S53). After acquiring the certificate issue history, the acquisition unit 33 stores the certificate issue history into the storage unit 40 (Yes in step S53).

The determination unit 34 determines whether IDs and the number of received certificates coincide with the certificate issue history (step S54). When IDs and the number of the received certificates do not coincide with the certificate issue history, the determination unit 34 determines there is a possibility that part of the certificates is hidden (No in step S54, step S55). The application processing unit 35 ends the processing without conducting processing such as decrypting certificates.

On the other hand, when IDs and the number of the received certificates coincide with the certificate issue history, the determination unit 34 determines there is no possibility that part of the certificates is hidden (Yes in step S54). When the acquisition unit 33 has determined there is no possibility that part of the certificates is hidden, the acquisition unit 33 may request the node 5 for a public key associated with each issuer ID by using issuer IDs contained in the certificate issue history received from the node 5.

The node 5 retrieves public key information (FIG. 4) in the distributed ledger 2 using issuer ID received from the communication apparatus 10 as a key. For example, it is supposed that public keys are requested for issuer ID=IDA and issuer ID=IDB. In the public key information, issuer ID=IDA is associated with a public key=KeyPA and issuer ID=IDB is associated with a public key=KeyPB. The node 5 notifies the communication apparatus 10 of KeyPA as the public key for issuer ID=IDA and notifies the communication apparatus 10 of KeyPB as the public key for issuer ID=IDB. The acquisition unit 33 acquires the public key for decrypting the certificate by receiving the notification from the node 5 through the reception unit 22 (step S56). The application processing unit 35 decrypts the certificate using the public key acquired the processing of the acquisition unit 33 to conduct certificate verification processing (step S57).

As described above, in the system according to the first embodiment, since certificate issue information is recorded into the distributed ledger 2 in association with category ID every time a certificate is issued, issue information on all certificates is registered in the distributed ledger 2. Each certificate is issued after a user registers, in the distributed ledger 2, a category ID which is capable of uniquely specifying the combination of the user or the communication apparatus 10 used by the user and the category of the certificate. This makes it possible for a service provider to identify whether a service user has submitted, to the provider, all digital certificates the user acquired for the category related to the service, by using the record of the distributed ledger 2.

Second Embodiment

In the first embodiment, since category ID of a user who is about to use the service is recorded in the distributed ledger 2, it is possible for a third party who is able to access information in the distributed ledger 2 to acquire certificate issue information on the user. Hence, protection for the privacy of the user is insufficient. There is also a risk that a third party who acquired certificate issue information to abuse the certificate issue information. In view of this, in the second embodiment, an embodiment in the case where category ID is encrypted such that a third party does not identify the user from the certificate issue information.

FIG. 9 is a diagram describing an example of key information used for encrypting category ID of the user C. In the second embodiment, the communication apparatus 10 is supposed to have stored key information for encrypting category ID as illustrated in FIG. 9. Regarding the key information for encrypting category ID, neither the secret key nor the public key is registered in the distributed ledger 2. For this reason, the communication apparatus 10 distributes a public key for decrypting encrypted category ID to the communication apparatuses 10 that issue and verify certificates. For example, key information for encrypting category IDs is kept by the communication apparatus 10 which has generated the key information so that a third party does not acquire a public key used for decrypting the category ID.

In the example of FIG. 9, a secret key KeyA is used to encrypt category ID for specifying the medical history of the user C. On the other hand, KeyB is used to decrypt data obtained by encrypting category ID for specifying the medical history of the user C. A secret key KeyC is used to encrypt category ID for specifying the educational attainment of the user C, and KeyD is used to decrypt data obtained by encrypting category ID for specifying the educational attainment of the user C.

Figure 10:
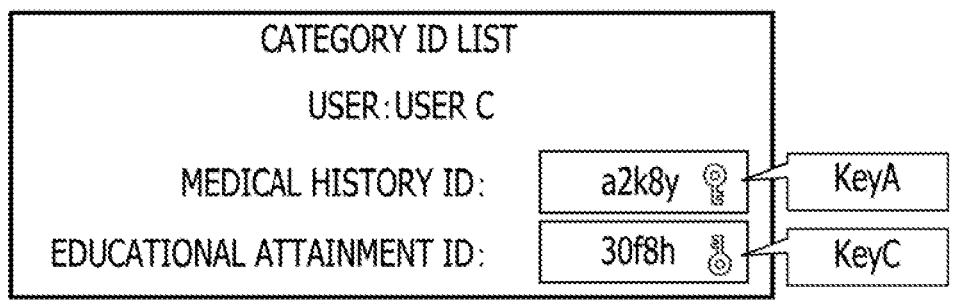
FIG. 10 is a diagram describing an example of a category ID list used in a second embodiment.

FIG. 10 is a diagram describing an example of a category ID list used in the second embodiment. In the second embodiment, information on a user who uses category ID and information obtained by encrypting category ID of each category are recorded in the category ID list which is registered into the distributed ledger 2. For example, information obtained by encrypting category ID (a2k8y) with the secret key KeyA is registered as the medical history ID of the user C. Similarly, information obtained by encrypting category ID (30f8h) with the secret key KeyC is registered as the educational attainment ID of the user C. In the following description, in order to make it easy to distinguish from category ID in a plain text, category ID encrypted is sometimes referred to as "encrypted ID".

Figure 11:
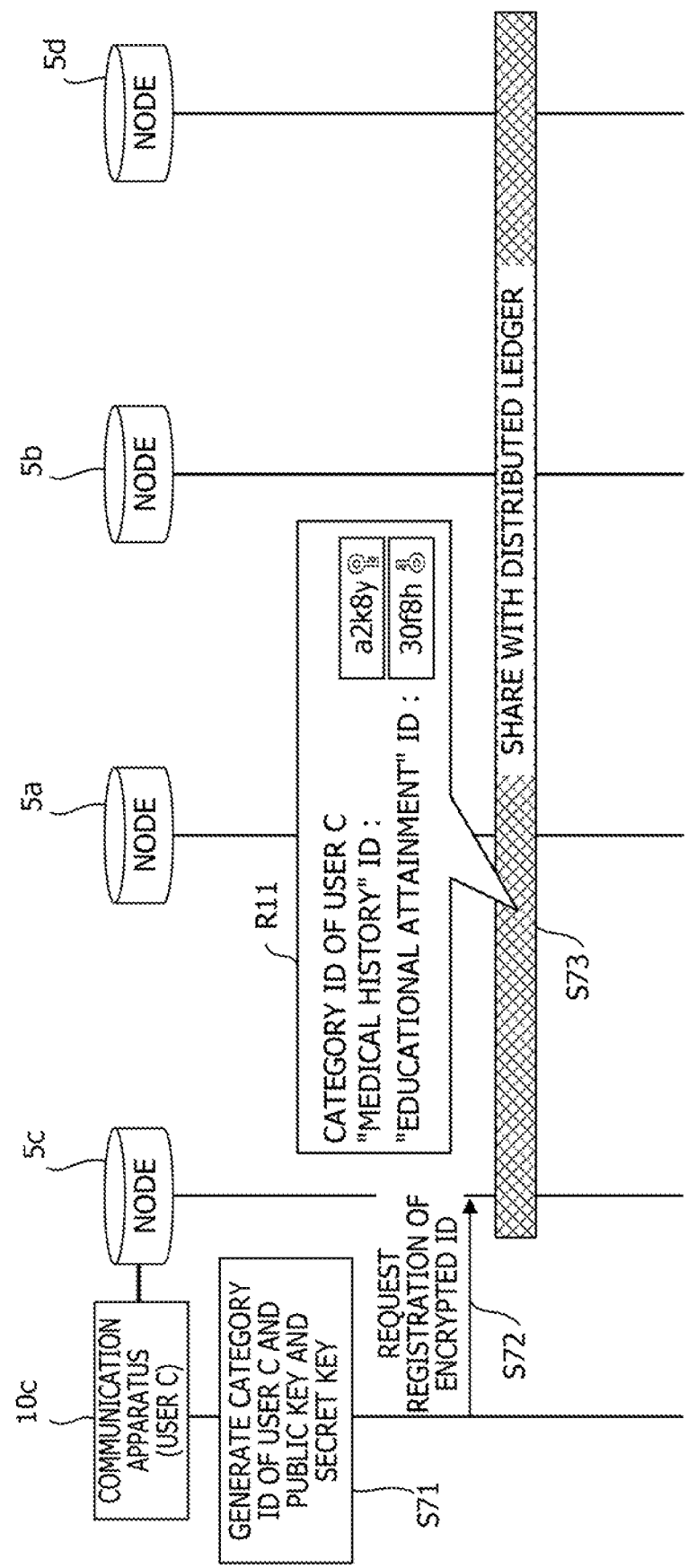
FIG. 11 is a sequence diagram describing an example of registration processing of category ID.

FIG. 11 is a sequence diagram describing an example of registration processing of category ID. The ID generation unit 31c of the communication apparatus 10c generates category ID which is capable of uniquely specifying the combination of the user C and the category, and a pair of a secret key and a public key use for encrypting category ID (step S71). The method of generating category ID is the same as that in the first embodiment. In the following description as well, it is supposed that a2k8y has been generated as category ID (medical history ID) which is capable of uniquely specifying the combination of the user C and the medical history, and 30f8h has been generated as category ID (educational attainment ID) which is capable of uniquely specifying the combination of the user C and the educational attainment. The method of generating a secret key and a public key used for encrypting category ID may be any known method. In the following description, it is supposed that a pair of keys illustrated in FIG. 9 has been generated. The ID generation unit 31c encrypts the generated category ID with the secret key generated for encrypting the category ID. Hence, the ID generation unit 31c encrypts the medical history ID (a2k8y) of the user C with the secret key KeyA and encrypts the educational attainment ID (30f8h) of the user C with the secret key KeyC.

The registration processing unit 32c of the communication apparatus 10c requests the node 5c to register category ID encrypted by the ID generation unit 31c (encrypted ID) into the distributed ledger 2 (step S72). The node 5c records each of encrypted IDs requested to be registered into the distributed ledger 2 in association with each category and information on the user. Information indicated in R11 of FIG. 11 is registered into the distributed ledger 2. The information indicated in R11 is shared among the nodes 5a to 5d using the distributed ledger 2 (step S73).

In the second embodiment as well, the form of registration may be changed depending on the implementation. For example, encrypted ID may be generated and recorded as information which is capable of uniquely specifying the combination of identification information of the communication apparatus 10 used by the user and the category.

Figure 12:
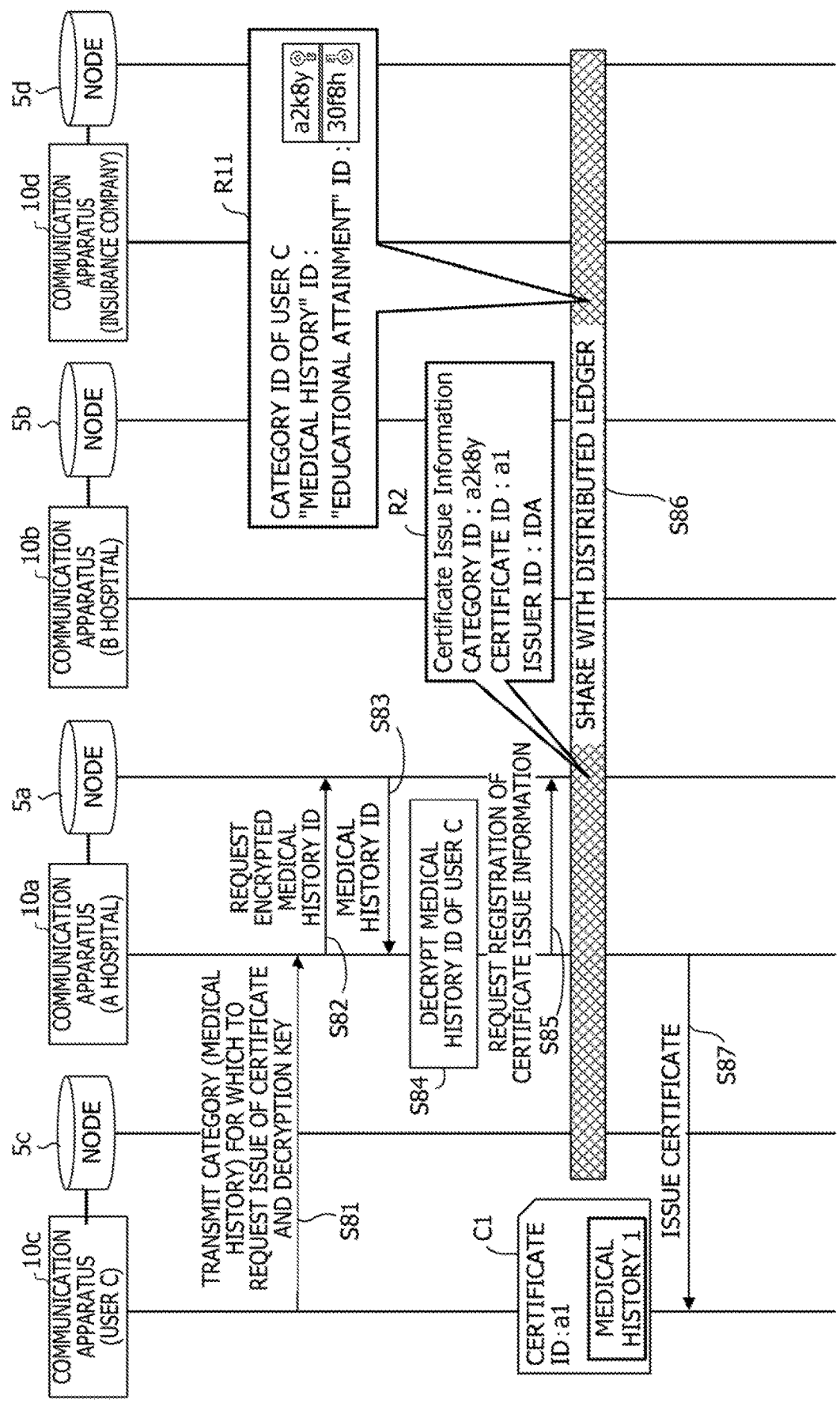
FIG. 12 is a sequence diagram describing an example of processing conducted when a certificate is issued.

FIG. 12 is a sequence diagram describing an example of processing conducted when a certificate is issued. With reference to FIG. 12, an example of processing in the case where the medical history certificate of the user C is issued by the communication apparatus 10a of the A hospital is described.

When recognizing the acquisition of the medical history certificate from the A hospital is requested by input from the user C or the like, the application processing unit 35c of the communication apparatus 10c generates a certificate request message containing information that the category for which the certificate is requested is medical history. The application processing unit 35c transmits the request message together with the public key associated with the category (medical history) for which the certificate is requested to the communication apparatus 10a through the transmission unit 21c (step S81). In step S81, KeyB is transmitted as the public key for decryption.

The acquisition unit 33a of the communication apparatus 10a acquires the request message through the reception unit 22a. The acquisition unit 33a then requests the node 5a for the encrypted medical history ID associated with the user C and category=medical history (step S82). The node 5a acquires the encrypted medical history ID associated with the medical history of the user C by referring to the record R11 (FIG. 11) contained in the distributed ledger 2 and notifies the communication apparatus 10a of the encrypted medical history ID (step S83). The acquisition unit 33a decrypts the encrypted medical history ID with KeyB (step S84). In the case where the acquisition unit 33a has succeeded in decryption, a correct decryption key has been sent from the source requesting the issue of the certificate, and it is thus considered that the issue of the certificate is requested from the communication apparatus 10c used by the user C. In the example of FIG. 12, the acquisition unit 33a is supposed to have acquired a2k8y as category ID for specifying the medical history of the user C by the decryption processing using KeyB.

The acquisition unit 33a of the communication apparatus 10a notifies the application processing unit 35a that the medical history certificate of the user C is requested and that category ID that specifies the medical history of the user C is a2k8y. The generation of the certificate and the generation of certificate ID in the application processing unit 35a are conducted in the same manner as in the first embodiment. Hereinafter, in the example of FIG. 12 as well, it is supposed that the application processing unit 35a has generated the certificate C1 on the medical history of the user C. Certificate ID for identifying the certificate C1 is supposed to be a1. The registration processing unit 32a requests the node 5a to register the certificate issue information into the distributed ledger 2 in the same processing as in the first embodiment (step S85). The node 5a is also supposed to have recorded the following information into the distributed ledger 2 in the same processing as in the first embodiment as certificate issue information (R2 of FIG. 12).

Certificate Issue Information
Category ID: a2k8y
Certificate ID: a1
Issuer ID: IDA Since the distributed ledger 2 is shared among the nodes 5a to 5d, the certificate issue information indicated in R2 is also shared among the nodes 5a to 5d like the encrypted ID information indicated in R11 (step S86). In the second embodiment as well, category ID contained in the certificate issue information is category ID in a plain text in the same manner as in the first embodiment. The registration information of category ID of the user contains only the encrypted ID as indicated in R11. For this reason, a third party who does not have the public key for decrypting the encrypted ID is not allowed to recognize to which user and to which category the category ID contained the certificate issue information contained in R2 relates even when acquiring information in the distributed ledger 2. For example, the third party does not recognize that the certificate issue information recorded in R2 is the medical history certificate of the user C. Thus, the privacy of the user C is protected even though the certificate issue information is recorded in the distributed ledger 2.

Thereafter, the application processing unit 35a of the communication apparatus 10a encrypts the certificate C1 generated for the medical history of the user C with the certificate generating secret key 42a and transmits the encrypted certificate C1 to the communication apparatus 10c (step S87). The encryption and transmission processing of the certificate are conducted in the same processing as in the first embodiment.

The processing described with reference to FIG. 12 is an example, and the generation of a certificate, the registration of certificate issue information, the transmission of a certificate may be conducted in the other communication apparatuses 10 such as the communication apparatus 10b in the same manner. The processing for any user other than the user C may be conducted in the same manner. The procedure of the processing described with reference to FIG. 12 may be changed depending on the implementation. For example, the transmission processing of the certificate in step S87 may be conducted in parallel with the processing in steps S85, S86, or may be conducted before the processing in steps S85, S86.

Figure 13:
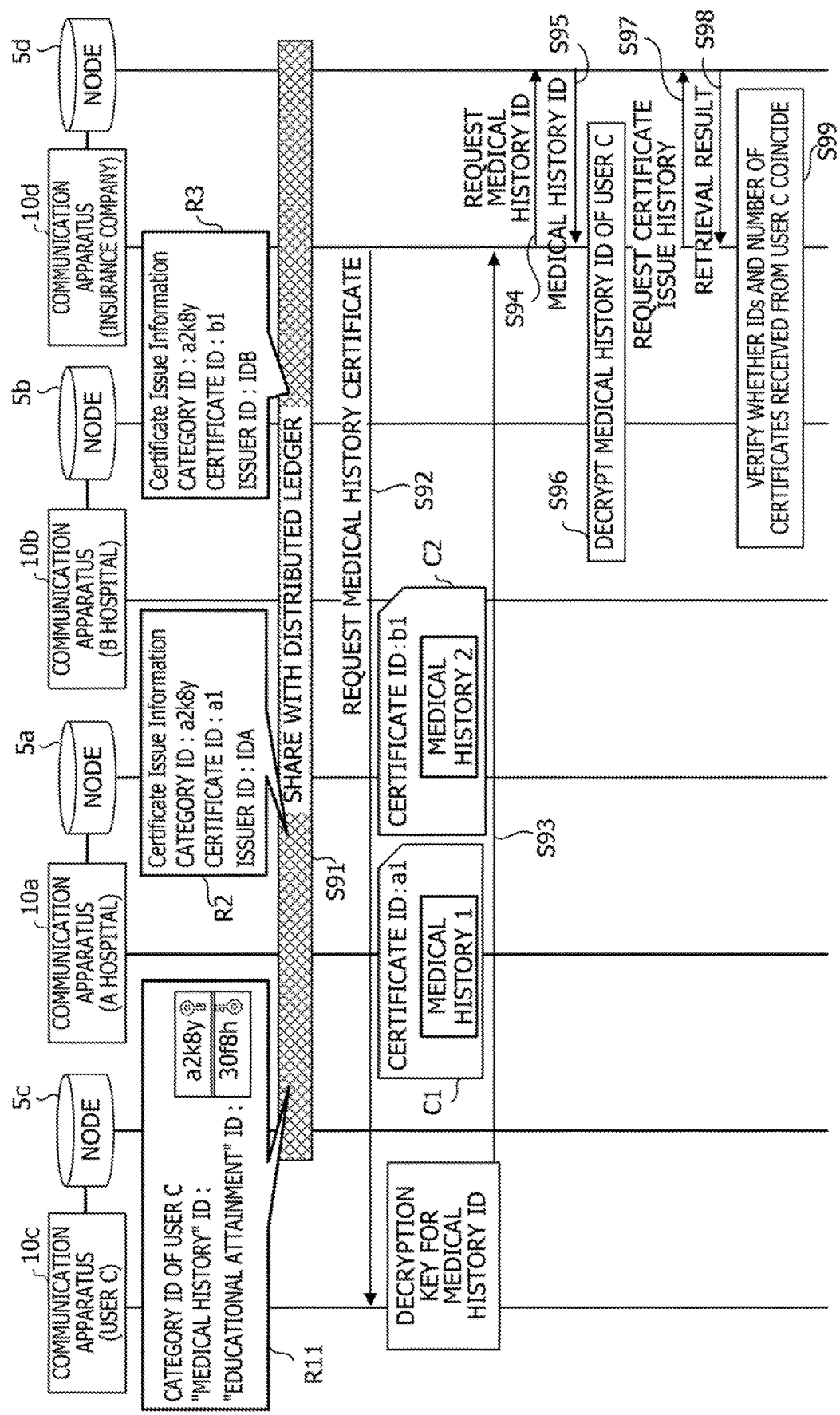
FIG. 13 is a sequence diagram describing an example of verification processing on completeness of a certificate.

FIG. 13 is a sequence diagram describing an example of the verification processing on completeness of a certificate. With reference to FIG. 13, an example of processing conducted in the case where the medical history certificates of the user C are issued from the A hospital and the B hospital, and the user C submits the medical history certificates to an insurance company is described. In FIG. 13, it is supposed that the following information has also been recorded in the distributed ledger 2 by the issue of the certificate C2 from the B hospital after the processing in step S86 of FIG. 12 (R3 in FIG. 13).

Certificate Issue Information
Category ID: a2k8y
Certificate ID: b1
Issuer ID: IDB The information in the distributed ledger 2 is shared among the nodes 5a to 5d (step S91).

It is supposed that in FIG. 13 as well, the user C applied for an insurance service to the insurance company. The operator of the insurance company transmits a send request for the medical history certificate from the communication apparatus 10d to the communication apparatus 10c used by the user C (step S92).

It is supposed that after the reception unit 22c of the communication apparatus 10c receives the send request, the application processing unit 35c conducts the display processing of the display screen corresponding to the send request. It is supposed that the certificate C1 issued from the A hospital, the certificate C2 issued from the B hospital, and the public key (KeyB) used for decrypting the medical history ID of the user C have been transmitted to the communication apparatus 10d by the operation of the user C (step S93). Information indicating that the transmitted certificates are the medical history certificates of the user C may be transmitted together to the communication apparatus 10d. Both the certificates C1 and C2 transmitted to the communication apparatus 10d in step S93 have been transmitted to the communication apparatus 10d in the state of encrypted data encrypted at the issuer of the certificates.

It is supposed that the application processing unit 35d of the communication apparatus 10d has acquired the certificate C1, the certificate C2, and the public key KeyB through the reception unit 22d. The application processing unit 35d stores the obtained information into the storage unit 40 as appropriate. The acquisition unit 33d inquires about the encrypted medical history ID associated with the user C and category=medical history to the node 5d (step S94).

The node 5d acquires the encrypted medical history ID associated with the medical history of the user C by referring to the distributed ledger 2 in response to the inquiry from the acquisition unit 33d of the communication apparatus 10d and notifies the communication apparatus 10d of the encrypted medical history ID (step S95). The acquisition unit 33d decrypts the encrypted medical history ID with KeyB (step S96). In the case where the acquisition unit 33d has succeeded in decryption, a correct decryption key has been sent from the source requesting the issue of the certificate, and it is thus considered that the certificate and the like have been transmitted from the communication apparatus 10c used by the user C. In the example of FIG. 13, the acquisition unit 33d is supposed to have acquired a2k8y as category ID for specifying the medical history of the user C by the decryption processing using KeyB. Next, the acquisition unit 33d requests the node 5d for a certificate issue history on the medical history ID of the user C (a2k8y) (step S97).

The node 5d retrieves certificate issue information associated with category ID=a2k8y in the distributed ledger 2 in response to the inquiry from the acquisition unit 33d of the communication apparatus 10d. In the example of FIG. 13, since category ID=a2k8y is contained in the issue information R2 and the issue information R3, the node 5d transmits the following retrieval result to the communication apparatus 10d as certificate issue history (step S98).

Issue information 1
Certificate ID=a1, issuer ID=IDA
Issue information 2
Certificate ID=b1, issuer ID=IDB The acquisition unit 33d of the communication apparatus 10d outputs the certificate issue history acquired from the node 5d through the reception unit 22d to the storage unit 40d and the determination unit 34d as appropriate. The determination unit 34d verifies whether ID and the number are coincident between the acquired certificate issue history and the certificates transmitted from the user (step S99). The processing such as the verification processing and decrypting each certificate when the verification in step S99 was succeeded is conducted in the same processing as that described in the first embodiment with reference to FIGS. 7 and 8. The communication method according to the second embodiment makes it possible for a service provider to check whether a certificate is hidden as in the first embodiment while protecting the privacy of a user who acquires a certificate.

Figure 14:
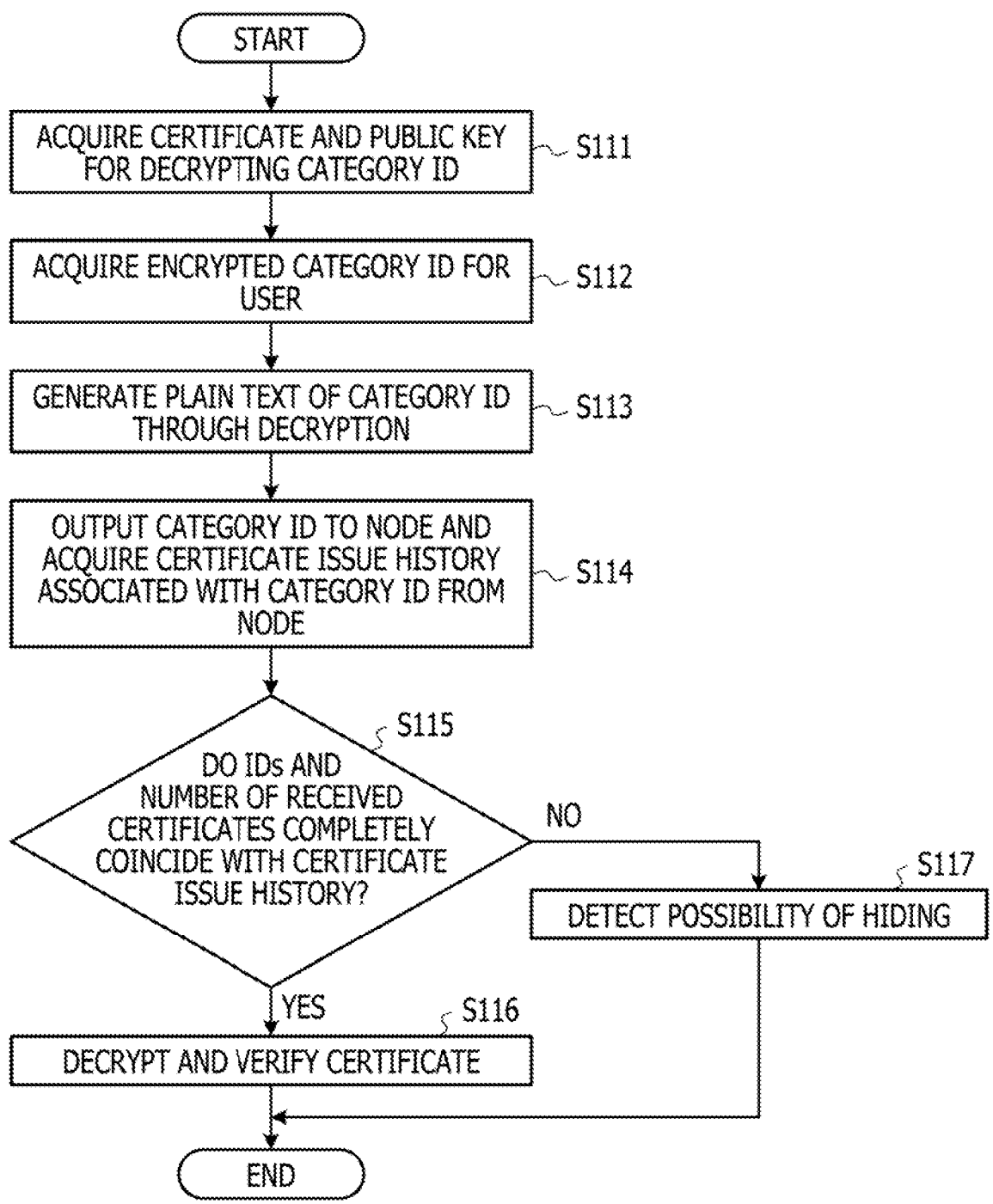
FIG. 14 is a flowchart describing an example of verification processing conducted by the communication apparatus.

FIG. 14 is a flowchart describing an example of verification processing conducted by the communication apparatus 10. FIG. 14 is an example of the processing, and may be changed depending on the implementation.

The application processing unit 35 of the communication apparatus 10 acquires a certificate and a public key for decrypting category ID (step S111). The application processing unit 35 stores the acquired information into the storage unit 40 as appropriate. The acquisition unit 33 acquires encrypted category ID for the user who has transmitted the certificate through the node 5 (step S112). The acquisition unit 33 generates a plain text of category ID by decrypting the encrypted category ID using the public key (step S113). The acquisition unit 33 acquires certificate issue history associated with the generated category ID in the plain text from the node 5 (step S114).

The determination unit 34 determines whether IDs and the number of received certificates completely coincide with the certificate issue history (step S115). When IDs and the number of the received certificates do not coincide with the certificate issue history, the determination unit 34 determines there is a possibility that part of the certificates is hidden (No in step S115, step S117). The application processing unit 35 ends the processing without conducting processing such as decrypting certificates.

On the other hand, when IDs and the number of the received certificates coincide with the certificate issue history, the determination unit 34 determines there is no possibility that part of the certificates is hidden (Yes in step S115). When it is determined there is no possibility that part of the certificates is hidden, the acquisition unit 33 decrypts and verifies the certificates (step S116). The detail of the processing in step S116 is the same as the processing described with reference to steps S56, S57 of FIG. 8.

Figure 15:
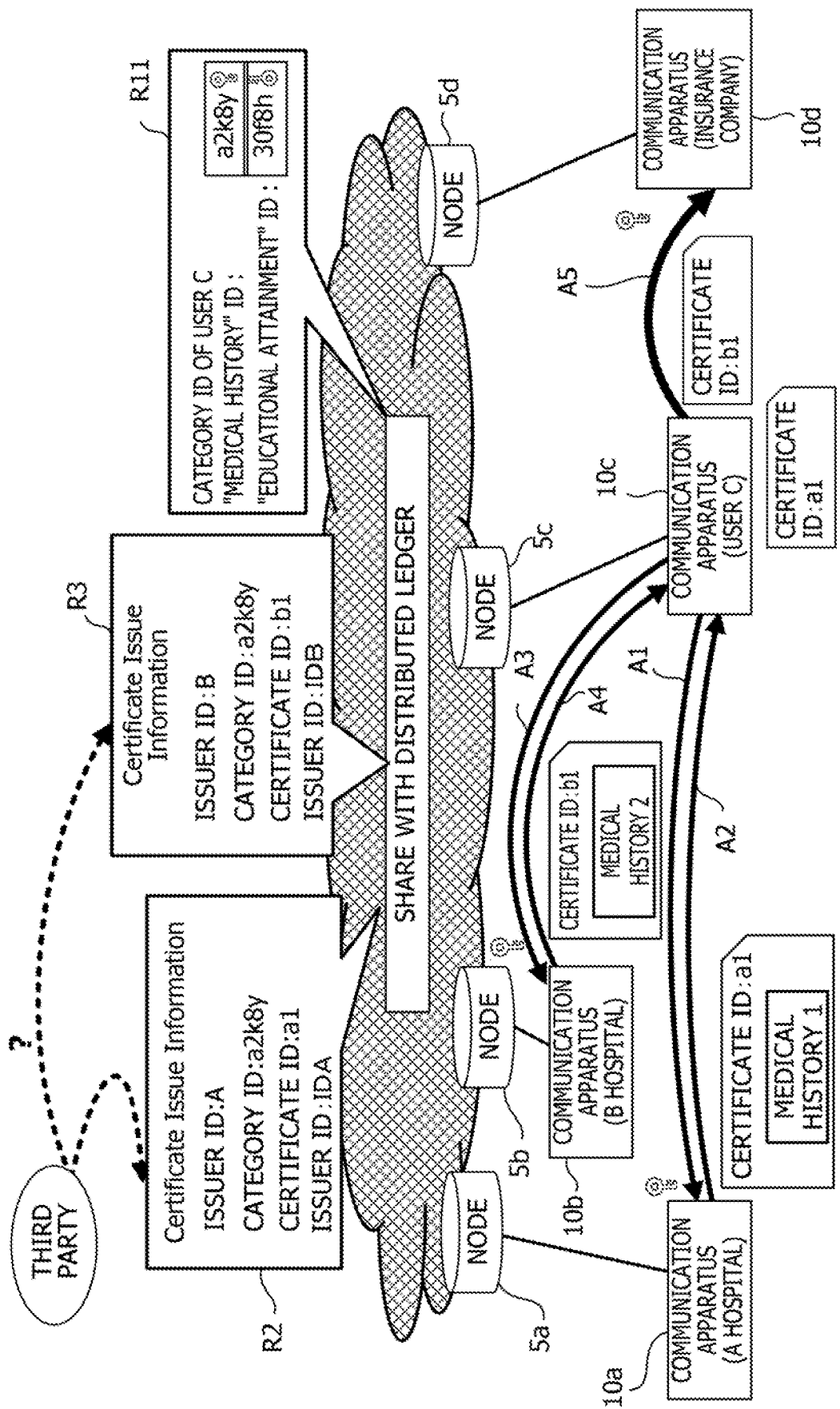
FIG. 15 is a diagram describing an example of communication processing in the second embodiment.

FIG. 15 is a diagram describing an example of communication processing in the second embodiment. With reference to FIG. 15, the effects achieved in the second embodiment are described. As illustrated in FIG. 15, in the second embodiment, each piece of certificate issue information contains the plain text of category ID, the certificate ID, and the issuer ID as indicated in R2 and R3. The registration of category ID of each user is conducted using the encrypted ID as indicated in R11. For this reason, a third party who has not acquired a public key paired with a secret key used for encrypting the encrypted ID is not allowed to recognize category ID of each user. For example, since a third party has not acquired a public key, the third party is not allowed to specify category ID of the user C even when reading R11 contained in the distributed ledger 2. Hence, even when looking at certificate issue information of R2, R3, or the like, the third party only finds that a certificate has been issued in association with category ID=a2k8y, and is not allowed to recognize that the certificate of the user C has been issued. For this reason, the use of the second embodiment makes it possible to protect the privacy of the user.

On the other hand, the use of the second embodiment makes it possible in the communication apparatus 10d to determine whether all digital certificates for a category use for application have been submitted by the user as in the case of the first embodiment. For example, the communication apparatus 10c of the user C presents the public key for decrypting category ID to the communication apparatus 10 which issues a certificate, as indicated by arrows A1, A3. It is possible for both of the communication apparatuses 10a, 10b to decrypt category ID using the public key, and to issue a certificate in association with the decrypted category ID and record issue information into the distributed ledger 2. Both of the communication apparatuses 10a, 10b transmit issued certificates to the communication apparatus 10c of the user (arrows A2, A4). Hence, it is possible for the communication apparatus 10c to transmit the public key used for decrypting category ID together with the acquired certificates to the communication apparatus 10d of the insurance company (arrow A5). In the communication apparatus 10d of the insurance company, it is possible to decrypt category ID using the public key like the communication apparatus 10a and the like, and acquire certificate IDs of the certificates recorded in the distributed ledger 2 in association with the decrypted category ID. For this reason, it is possible for the communication apparatus 10d to determine whether there is a possibility that digital certificates are hidden by comparing the certificate IDs of the certificates recorded in the distributed ledger 2 in association with the decrypted category ID and certificate IDs of certificates presented from the communication apparatus 10c.

<Others>

The embodiments are not limited to the above, and may be variously modified. Some examples thereof will be described below.

The formats of the tables, messages, digital certificates, and the like described above are only examples, and may be changed depending on the implementation. For example, tables, messages, and digital certificates may include information elements other than the information elements described above, and may not include some of the illustrated information elements.

In the above-description, a case where the category is medical history has been described as an example, the category of a certificate to be transmitted and received in the communication methods according the embodiments may be changed as appropriate depending on the implementation. For example, the category may be educational attainment, personal history, criminal record, or the like.

Although the above description has been made while the processes conducted by the communication apparatus 10 are separated, any of the communication apparatuses 10 may conduct the generation of category ID, the issue of digital certificate, the transmission, and the verification. In the second embodiment, any of the communication apparatuses 10 may conduct the encryption of category ID, the generation of category ID, the issue of digital certificate, the transmission, and the verification.

In the above description, although the case where the communication apparatuses 10 are not apparatuses that share the distributed ledger 2 has been described as an example, the node 5 and the communication apparatus 10 may be one apparatus. In the case where the node 5 and the communication apparatus 10 are implemented in one apparatus, the apparatus which issues a certificate issues a certificate and registers certificate issue information on the certificate issued by the apparatus into the distributed ledger 2. In this case, the apparatus the user is about to receive a service uses registers category ID into the distributed ledger 2. The apparatus which verifies a certificate specifies certificate issue history by accessing information in the distributed ledger 2, and may determine whether there is a possibility that a certificate has been hidden.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A first communication apparatus of accessing at least any one of a plurality of nodes sharing a distributed ledger, the first communication apparatus comprising:
a memory; and
a processor coupled to the memory, the processor being configured to:
receive one or more digital certificates regarding a user from a second communication apparatus, each of the one or more digital certificates being a digital certificate including first identification information and second identification information, the first identification information including an identification that identifies the corresponding digital certificate, the second identification information including an identification that identifies a combination of a category of the corresponding digital certificate and the user of the corresponding digital certificate;
obtain, from any of the plurality of nodes, by using the second identification information of the one or more digital certificates regarding the user, certificate issue history stored in the distributed ledger in association with the second information of the one or more digital certificates, the certificate issue history being information including one or more records regarding the one or more digital certificates, each of the one or more records being a record that has been recorded in response to issuing of a corresponding digital certificate of the one or more digital certificates and that indicates the first identification information of the corresponding digital certificate;

compare the one or more digital certificate and the certificate issue history to thereby output information based on a result of the comparing, the comparing being configured to determine whether any of the one or more records included in the certificate issue history indicates the first identification information is not identical to the one or more digital certificates; and in response that any of the one or more records included in the certificate issue history indicates the first identification information identical to none of the one or more digital certificates, output information indicating that there is a possibility that the one or more digital certificates do not include a digital certificate which has been issued for the category indicated in the second identification information of the one or more digital certificates.

2. The first communication apparatus according to claim 1, wherein the second identification information is generated before the user acquires the one or more digital certificates, each of the one or more digital certificates is generated in association with the second identification information, and the certificate issue history on each of the one or more digital certificates is recorded in the distributed ledger in association with the second identification information.

3. The first communication apparatus according to claim 1, wherein the distributed ledger stores encrypted information obtained by encrypting the second identification information with a secret key used by the second communication apparatus before the user acquires the one or more digital certificates, each of the one or more digital certificates is generated by an apparatus that has acquired a public key paired with the secret key from the second communication apparatus in association with the second identification information generated by decrypting the encrypted information with the public key, and the certificate issue history on each of the one or more digital certificates is recorded in the distributed ledger in association with the second identification information.

4. The first communication apparatus according to claim 3, wherein the processor is further configured to:

acquire the public key from the second communication apparatus, acquire the second identification information by decrypting the encrypted information with the public key, and acquire the certificate issue history associated with the second identification information.

5. A second communication apparatus of accessing at least any one of a plurality of nodes sharing a distributed ledger, the second communication apparatus comprising:

a memory; and a processor coupled to the memory, the processor being configured to:

obtain one or more digital certificates by performing first processing one or more times, the first processing including transmitting a request to any of the plurality of nodes to thereby cause the any of the plurality of nodes to perform second processing, the second processing including generating a digital certificate being any of the one or more digital certificates and registering a record with respect to the generated digital certificate to a certificate issue history, the generated digital certificate including first identification information and second identification information, the first identification information including an identification that identifies the generated digital certificate, the second identification information including an identification that identifies a combination of a category of the generated digital certificate and a user of the generated digital certificate, the request including the second identification information, the certificate issue history being stored in the distributed ledger in association with the second identification information, and receiving the generated digital certificate from the any of the plurality of nodes; and transmit the one or more digital certificates to a first communication apparatus to thereby cause the first communication apparatus to perform processing, the processing including:

obtaining, from any of the plurality of nodes, by using the second identification information of the one or more digital certificates, the certificate issue history stored in the distributed ledger in association with the second information of the one or more digital certificates, the certificate issue history being information including one or more records regarding the one or more digital certificates, each of the one or more records being a record that has been recorded in response to issuing of a corresponding digital certificate of the one or more digital certificates and that indicates the first identification information of the corresponding digital certificate;

comparing the one or more digital certificate and the certificate issue history to output information based on a result of the comparing, the comparing being configured to determine whether any of the one or more records included in the certificate issue history indicates the first identification information is not identical to the one or more digital certificates; and in response that any of the one or more records included in the certificate issue history indicates the first identification information identical to none of the one or more digital certificates, output information indicating that there is a possibility that the one or more digital certificates do not include a digital certificate which has been issued for the category indicated in the second identification information of the one or more digital certificates.

6. A communication method implemented by a system including a first communication apparatus and a second communication apparatus, each of the first and second communication apparatuses being configured to communicate with at least any one of a plurality of nodes, each of the plurality of nodes sharing a distributed ledger with each other via a network, the communication method comprising:

causing the second communication apparatus to obtain one or more digital certificates by performing first processing one or more times, the first processing including transmitting a request to any of the plurality of nodes to thereby cause the any of the plurality of nodes to perform second processing, the second processing including generating a digital certificate being any of the one or more digital certificates and registering a record with respect to the generated digital certificate to a certificate issue history, the generated digital certificate including first identification information and second identification information, the first identification information including an identification that identifies the generated digital certificate, the second identification information including an identification that identifies a combination of a category of the generated digital certificate and a user of the generated digital certificate, the request including the second identification information, the certificate issue history being stored in the distributed ledger in association with the second identification information, and receiving the generated digital certificate from the any of the plurality of nodes;

causing the second communication apparatus to transmit the one or more digital certificate to thereby cause the first communication apparatus to receive the one or more digital certificates;

causing the first communication apparatus to obtain, from any of the plurality of nodes, by using the second identification information of the one or more digital certificates, the certificate issue history stored in the distributed ledger in association with the second information of the one or more digital certificates, the certificate issue history being information including one or more records regarding the one or more digital certificates, each of the one or more records being a record that has been recorded in response to issuing of a corresponding digital certificate of the one or more digital certificates and that indicates the first identification information of the corresponding digital certificate;

causing the first communication apparatus to compare the one or more digital certificate and the certificate issue history to thereby output information based on a result of the comparing, the comparing being configured to determine whether any of the one or more records included in the certificate issue history indicates the first identification information is not identical to the one or more digital certificate; and in response that any of the one or more records included in the certificate issue history indicates the first identification information identical to none of the one or more digital certificates, output information indicating that there is a possibility that the one or more digital certificates do not include a digital certificate which has been issued for the category indicated in the second identification information of the one or more digital certificates.

* * * * *